US009782548B2

(12) United States Patent
Shivkumar et al.

(10) Patent No.: US 9,782,548 B2
(45) **Date of Patent: *Oct. 10, 2017**

(54) ENDOVASCULAR CATHETER AIR BLOCK

(71) Applicant: The Regents of the University of California, Oakland, CA (US)

(72) Inventors: Kalyanam Shivkumar, Los Angeles, CA (US); David A. Cesario, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 870 days.

This patent is subject to a terminal disclaimer.

(21) Appl. No.: 13/785,964

(22) Filed: Mar. 5, 2013

(65) Prior Publication Data

US 2013/0289526 A1 Oct. 31, 2013

Related U.S. Application Data

(63) Continuation of application No. 12/162,474, filed as application No. PCT/US2006/043149 on Nov. 3, 2006, now Pat. No. 8,419,685.

(Continued)

(51) Int. Cl.
*A61M 1/00* (2006.01)
*A61M 5/178* (2006.01)

(Continued)

(52) U.S. Cl.
CPC .............. *A61M 5/36* (2013.01); *A61M 5/385* (2013.01); *A61M 39/06* (2013.01); *A61M 39/10* (2013.01);

(Continued)

(58) Field of Classification Search
CPC ........ A61M 5/36; A61M 5/385; A61M 39/06; A61M 39/10

(Continued)

(56) References Cited

U.S. PATENT DOCUMENTS 7,279,031 B1 * 10/2007 Wright ................ A61M 1/3627 604/126
8,419,685 B2 * 4/2013 Shivkumar ........... A61M 5/385 604/122

(Continued)

FOREIGN PATENT DOCUMENTS

EP 1160002 A2 12/2001

OTHER PUBLICATIONS

European Office Action re European Patent Application No. 06 827541.1 dated Mar. 7, 2013.

*Primary Examiner* — Matthew F Desanto
(74) *Attorney, Agent, or Firm* — Knobbe, Martens, Olson & Bear LLP

(57) ABSTRACT

This invention is an air block for industrial, medical, and non-medical uses. For example, the air block is connected to the proximal end of a vascular access catheter. The air block is either removably connected to the proximal end of the catheter or it is integral to the proximal end of the catheter. The air block permits introduction of other catheters or instrumentation through its central lumen and on into a lumen of the catheter while minimizing fluid loss or gain into the catheter. The air block further prevents air from entering the catheter and provides for removal of the air or other gas from the central lumen before it can enter the catheter where it could cause harm to the patient. The air block can be attached to various standard proximal catheter terminations including Luer fittings and hemostasis valve outer barrels.

11 Claims, 13 Drawing Sheets

604 512 502 612 504 602 510 610 506 508 600 524 602 514 604

Related U.S. Application Data

(60) Provisional application No. 60/763,604, filed on Jan. 30, 2006.

(51) Int. Cl.
*A61M 5/36* (2006.01)
*A61M 5/38* (2006.01)
*A61M 39/06* (2006.01)
*A61M 39/10* (2006.01)
*B01D 19/00* (2006.01)

(52) U.S. Cl.
CPC . *B01D 19/0031* (2013.01); *A61M 2205/7536* (2013.01)

(58) Field of Classification Search
USPC .................................................. 604/122, 126
See application file for complete search history.

(56) References Cited

U.S. PATENT DOCUMENTS

2002/0110485 A1 8/2002 Stringer et al.
2005/0027253 A1 * 2/2005 Castellano ........ A61M 25/0662 604/122
2005/0261619 A1 11/2005 Gay

* cited by examiner

ENDOVASCULAR CATHETER AIR BLOCK

CROSS-REFERENCE TO RELATED APPLICATIONS

This application is a continuation of the U.S. patent application Ser. No. 12/162,474, filed Aug. 21, 2009, which is the U.S. National Phase filing under 35 U.S.C. §371 of PCT/US2006/043149, filed Nov. 3, 2006, which designated the United States and was published in English, which claims priority to U.S. Provisional Patent Application No. 60/763,604, filed Jan. 30, 2006. The contents of these applications are incorporated herein by reference in their entireties.

FIELD

The disclosure relates to devices and methods for blocking gases for industrial purposes such as during access to vessels, chambers, canals or containers, or for medical purposes such as during access to the cardiovascular system or other body vessels or lumens, especially procedures performed in the fields of cardiology, radiology, electrophysiology, and surgery.

BACKGROUND

During certain interventional procedures that require vascular access, the patient is catheterized through a vein or artery and a catheter is routed to the heart or other region of the cardiovascular system. The initial steps involve placement of a hollow tube within the blood vessel. The hollow tube can be a sheath or catheter. In many cases, these catheters or sheaths are fairly long. Catheters or other devices are routinely routed through these sheaths into the arterial side of the circulatory system where pulsatile blood pressure generally averages 100 mm Hg cycles and pulses at an average rate of approximately 1 to 3 beats per second. The peak systolic pressures in the arterial side in a normal patient are around 110 to 130 mm Hg and the lowest diastolic pressures are around 70 to 90 mm Hg. In a hypertensive patient experiencing what is known as high blood pressure, the peak systolic arterial pressure can exceed 250 mm Hg. A catheterization lab or operating room is typically a clean room, which is maintained at positive pressure ranging from 0 to 2 mm Hg. When a catheter is routed into the arterial system, the distal end of a through lumen will be exposed to these arterial blood pressures and a positive pressure gradient will exist between the distal end and the proximal end of the catheter can be such that, unless proper hemostasis is maintained, blood is forced out through the catheter into the ambient environment.

There are an increasing number of cases where a sheath is routed to the venous side. Its distal end is exposed to central venous blood pressure, which cycles at the same rate as the arterial side, approximately 1 to 3 beats per second. The normal, healthy, pulsatile venous pressures are lower than those in the arterial side and can range between low values of around 3 to 5 mm Hg and peak values of around 15 to 20 mm Hg with an average of approximately 10 mm Hg. Patients with ectopic beats or premature ventricular contractions can achieve nearly zero central venous pressure during part of the cardiac cycle. Patients with tricuspid incompetence and conduction pathologies can experience right atrial pressures of −5 to −10 mm Hg. In the central venous circulation, for example, as measured in the right atrium of the heart, the distal end of the sheath can be exposed, during part or all of the cardiac cycle, to pressures equal to or below those to which the proximal end of the sheath is exposed. When the room or ambient pressure, to which the proximal end of the sheath is exposed, is above that of the distal end of the sheath, a negative pressure gradient or pressure drop can occur. Such a negative pressure drop allows air to be forced into the proximal end of the catheter. Should the air reach the distal end of the catheter by way of a through lumen, it could escape into the blood stream in the form of large or small bubbles, resulting an air embolism. Such air embolisms can cause harm to the health of the patient, or even death, and need to be avoided. This situation can be exacerbated by ambient room pressures often found in the cath lab. Under normal conditions, the environment of the clean room, operating theatre, or catheterization lab can be maintained at an elevated air pressure of around 5 to 10 mm Hg above exterior air pressure. Thus, a right atrial pressure, which momentarily dips to 2 mm Hg, can be overcome by a room air pressure of 2 to 3 mm Hg causing air to be forced retrograde through the catheter and into the circulatory system.

Typical arterial catheter procedures include percutaneous transluminal coronary angioplasty, coronary stenting, aortic stent-graft procedures, endarterectomy, and the like. In the United States, more than 500,000 of these arterial procedures are performed each year. The number of venous procedures being performed each year is increasing as more endovascular therapies evolve or are developed for pathologies such as atrial fibrillation, mitral valve repair, mitral valve replacement, and the like. There are currently more than 200,000 electrophysiology procedures performed in the right and left atrium of the heart annually in the United States. During a venous procedure, a catheter is routed through the venous circulation where low instantaneous, or pulsatile, pressures can occur. During the approach to the heart and in preparation for a trans-septal puncture, the distal end of the catheter can reside in the vena cava or right atrium for a substantial amount of time. Such positioning renders the catheter at risk for being exposed to a negative pressure drop and the potentially catastrophic consequences of retrograde air flow. An air embolism or bubble escaping into the venous circulation can lodge in the lungs causing a pulmonary embolism. Pressures in the left atrium are similar to those in the right atrium. Left atrial pressure is pulsatile and can have peak values of around 10 to 20 mm Hg and minimum values of between −5 and 5 mm Hg. Negative minimum pressures are experienced in patients with certain pathophysiologies such as aortic stenosis. These types of patients are often the ones who undergo catheterization procedures. Left sided (arterial) procedures, which are accessed from the right (or venous) side present a further complication in that a gas bubble or embolism that escapes into the arterial side can be pumped by the heart to sensitive tissues where it can lodge, prevent distal blood flow, and thus cause ischemia. Such ischemia is potentially life threatening if it occurs in the cerebrovasculature or the coronary arteries.

Current devices and methods prevent air entrainment into a sheath or catheter or for preventing blood escape from these sheaths or catheters involve the use of valves such as stopcocks, hemostasis valves, adjustable Tuohy-Borst valves, and the like. These devices are adequate at preventing the loss of substantial amounts of blood during arterial procedures. The current devices, however, are less well suited to preventing air backflow into the sheath or catheter and possibly into the patient. Instances can arise where a hemostasis valve breaks or becomes disconnected from the sheath or catheter and a substantial bolus of air can enter the cardiovascular system with sometimes catastrophic consequences. Even without such equipment failure, operator error can result in air being pumped retrograde into the blood stream by ambient air pressure, if a Tuohy-Borst valve is not properly adjusted, a hemostasis valve becomes distorted, or too small a catheter is used for the type of hemostasis valve.

There is a need for improved systems, devices, apparatus and methods for preventing air entrainment into a patient through catheters routed into the venous circulation. Such systems, devices, apparatus, and methods need to accept catheters or instrumentation through their central lumens and close the seal around those catheters better than current devices. The systems further need to close more quickly than the current systems when the inserted catheter is removed. The current systems need also to be improved to prevent air passage retrograde back into the catheter while still maintaining device operability.

SUMMARY OF THE INVENTION

An embodiment of this invention allow work in a medical environment wherein a pressure-differential is expected. Certain embodiments of the invention will prevent air from entering and/or the escape of blood or other body fluids when a high pressure system (defined as above atmospheric) is accessed by interventional techniques.

For example, disclosed in one embodiment is an air block, or air trap, module that is affixed to the proximal end of a primary sheath, said primary sheath intended for vascular access. The module is generally disposable and can be provided integral to the primary sheath, permanently attached to the primary sheath, or removably attached to the primary sheath. The module permits introduction of catheters or other instrumentation through the central lumen of the primary sheath. In one embodiment, the module further substantially prevents the loss of blood when the distal end of the catheter is exposed to circulating blood, either in the arterial or venous system. The module traps substantially any air entrained into its interior lumen, prevents the air from entering the through lumen of the primary catheter, and shunts the air out of the interior lumen of the module through an air exit port.

In other embodiments, the invention is applicable to industrial uses where the blocking of gasses is desired. For example, an embodiment of the invention prevents gas from entering and/or the escape of gas of other materials from a vessel when a high pressure system is accessed.

The air block comprises a main housing or shell, a catheter entry port, a catheter exit port, an inner channel further comprising perforations in its wall, a fluid inlet port, and a gas, or air, exit port. The catheter entry port further comprises a hemostasis valve such as, but not limited to, a slit valve, duckbill valve, Tuohy-Borst valve, or the like. The catheter exit port further comprises a hemostasis valve such as, but not limited to, a slit valve, a duckbill valve, a Tuohy-Borst valve, or the like. The catheter exit port also comprises a docking mechanism capable of securely affixing the air block to the proximal end of the primary sheath such that the catheter exit port and the inlet port of the primary catheter are concentric and aligned.

In other embodiments directed to industrial or non-medical uses, the catheter ports are replaced with a wide variety of different types of ports. Also, instead of a catheter, an embodiment of the invention can be adapted to receive a variety of devices such as tubular devices for insertion into containers, canals, vessels, passageways, or the like. Such devices can be designed, for example, to permit injection or withdrawal of fluids or to keep a passage open. For example, an embodiment of the invention directed to industrial uses prevents gas from entering and/or the escape of gas of other materials from a vessel when a device is inserted into the vessel.

Thus, while certain embodiments are described with respect to endovascular uses or a catheter, the invention is not so limited and can be configured for use in a variety of medical, non-medical and industrial uses where the blocking of gas is desired.

The air block, or air removal system, can be operably connected to an external subsystem that provides a reservoir of liquid such as water, saline, Ringers solution, or the like pressurized to a level above that of the venous pressure. The fluid delivery subsystem is operably connected to the fluid inlet port of the air block by way of a tube, manifold, or the like. The air block can also be operably connected to an external subsystem that withdraws or removes gas, specifically air, which can collect within the shell of the air block. The gas removal subsystem is operably connected to the shell of the air block by the gas removal port. Although the subsystems are referred to as being external, they can also be internal, integral to, or affixed to the air block module. In an embodiment, the gas removal subsystem can comprise a gas permeable membrane that permits gas such as air to pass but substantially prevents the loss of liquids such as water, saline, or blood. In this embodiment, a pump is operably connected to withdraw the air out of the trap through the as permeable membrane by generating a pressure drop within a range that facilitates such air passage.

The air block, in an embodiment, can comprise one way valves at the fluid inlet port and at the gas outlet port. These one-way valves permit flow only in a single direction and make sure that fluid can only flow into the air block from the fluid inlet port and that gas can only flow out of the gas outlet port. In another embodiment, the air block comprises an outer shell and a core tube, the core tube having either a straight tubular configuration or a central bulge directed radially outward from the axis of the tube. The core tube can further comprise perforations large enough to cause gas collected within the core tube to pass out into the surrounding area within the air block shell.

Another aspect of the invention is the method of use of the bubble, gas, or air block apparatus. The air block is affixed to the proximal end of the primary catheter, cannula, introducer, or sheath. The primary catheter is flushed with saline and purged of air. The primary catheter is introduced into the vascular system, generally after first placing a guidewire, which is routed through the central lumen of the air block. The fluid inlet port of the air block is connected to a source of normal saline. The gas outlet port of the air block can be connected to a fluid removal system. The primary catheter is routed to its target location. The secondary catheter, or catheters, can be inserted through the proximal most hemostasis valve of the air block, through the central lumen of the core tube of the air block, through the secondary air block hemostasis valve, through the catheter lumen and into the vascular system at the target site. Any air that becomes entrained into the core tube of the air escapes through perforations in the core tube and migrates into the larger diameter shell. The trapped air either remains within the larger diameter shell or it is drawn off by the fluid removal system either into the air or into an air reservoir. The fluid removal system can be optimized to selectively withdraw only gasses such as air. This selective withdrawal of air can be performed using a microporous membrane fabricated from materials such as, but not limited to, polypropylene, polyethylene, polytetraflouoroethylene, other polyolefin, polyester, or the like. The membrane can have porous structures that penetrate from one side of the membrane to the other and with a size of about 100 microns with a range of 50 microns to 1000 microns. The pore density and pore size can be selected to be compatible with a pressure drop across the membrane, as generated by a pump or other suction (vacuum) or pressure generating device so as to remove a given volume of air over a specified length of time without the loss of a substantial amount of liquid such as blood.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE PREFERRED EMBODIMENT

In accordance with current terminology pertaining to medical devices, the proximal direction will be that direction on the device that is furthest from the patient and closest to the user, while the distal direction is that direction closest to the patient and furthest from the user. These directions are applied along the longitudinal axis of the device, which is generally an axially elongate structure having one or more lumens or channels extending through the proximal end to the distal end and running substantially the entire length of the device. As defined herein, a sheath is an axially elongate tube that can also be termed a catheter, a cannula, an introducer, or the like.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Figure 1:
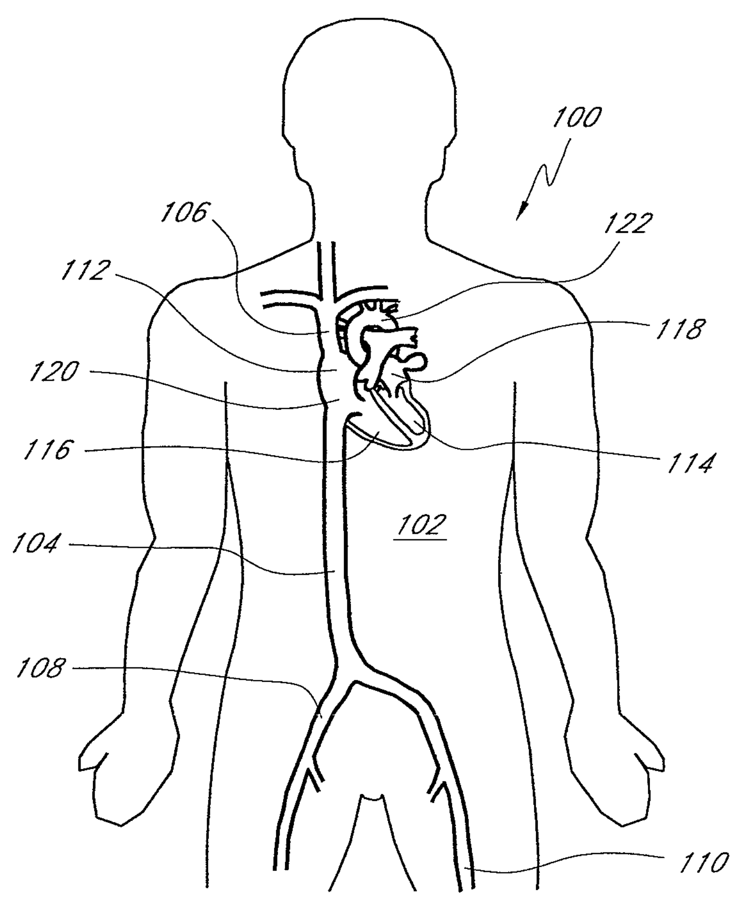
FIG. 1 illustrates a schematic view of the cardiovascular system of the human.

FIG. 1 illustrates a schematic diagram of a part of the circulatory system 102 of a human 100. The circulatory system 102 comprises a heart 112, an inferior vena cava 104, a superior vena cava 106, an iliac vein 108, and a femoral vein 110. The heart 112 further comprises a left ventricle 114, a right ventricle 116, a left atrium 118, a right atrium 120. The circulatory system 102 also comprises the aorta 122.

Referring to FIG. 1, all the functional components are operably connected to each other. The left ventricle 114 of the heart 112 pumps blood into the aorta 122 by muscular contraction of the myocardium. Blood enters the left ventricle 114 through the mitral valve from the left atrium 118. Blood is pumped from the right ventricle 116, through the pulmonary valve into the pulmonary artery. Blood enters the right ventricle 116 from the right atrium 120 through the tricuspid valve. All parts of the heart 112 and circulatory system 102 are integral to each other, although they are comprised of various types of tissue.

Figure 2:
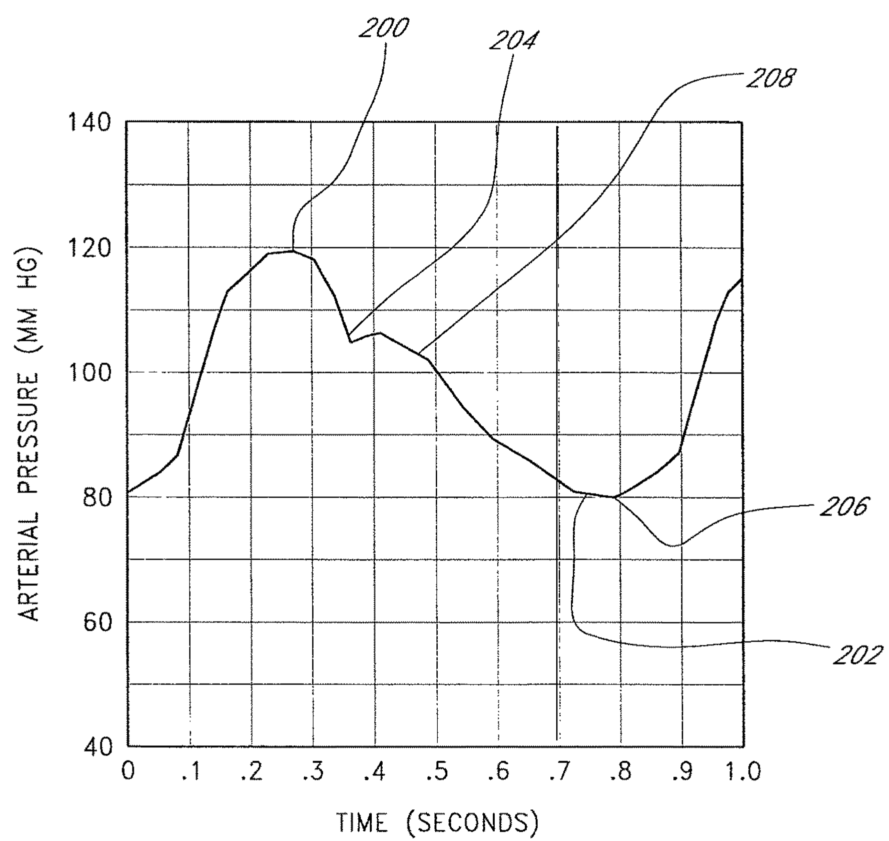
FIG. 2 illustrates a graph of the blood pressure within the arterial system at a location near the heart plotted against time.

FIG. 2 illustrates a plot of arterial pressure 200 as a function of time. The arterial pressure 200 is pulsatile and the waveform generally repeats itself each cardiac cycle. The end of the first cardiac cycle 202 is approximately 0.8 seconds following the beginning of the cycle. The arterial pressure waveform 200 has a maximum value 204, a minimum value 206, and a dicrotic notch 208.

Referring to FIG. 2, typical arterial or systemic pressure within the human circulatory system is a time varying value that appears somewhat like a triangle wave, having rounded peak and minimum curvature, with a maximum value 204 called the peak systolic pressure and the minimum value 206 called the minimum diastolic pressure. A small feature in the downsloping part of the wave is called the dicrotic notch 208 and is the hemodynamic remnant of the closure of the aortic valve.

Figure 3:
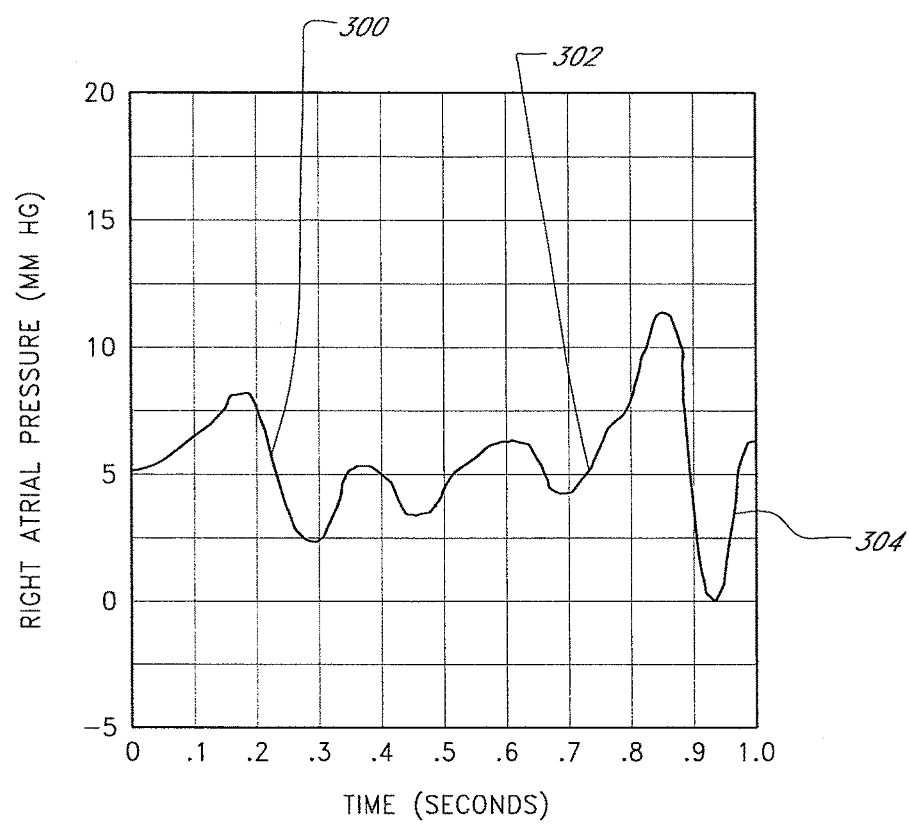
FIG. 3 illustrates a graph of the blood pressure within the venous system in the region of the right atrium, plotted against time.

FIG. 3 illustrates a plot of the right atrial pressure 300 as a function of time. The right atrial pressure 300 is pulsatile and the waveform generally repeats itself each cardiac cycle. The end of the first cardiac cycle 302 is approximately 0.74 seconds following the beginning of the cycle. The following partial cycle 304 illustrates a right atrial pressure tracing in a patient with an arrhythmia causing the minimum pressure to drop as low as 0 mm Hg.

Referring to FIG. 3, the right atrial pressure has a much lower mean value than that in the systemic circulation. The larger, first pressure pulse, within the right atrium, is generated by the contraction of the right atrium which increases pressure within the right atrium. A smaller, second pressure pulse is generated when the right ventricle contracts and causes the tricuspid valve to balloon backward into the right atrium. A third pressure pulse is caused by muscular or myocardial contraction of the heart. A second beat 304 begins at the end 302 of the first recorded cycle 300. The second beat 304 is the result of a heart experiencing electrical disturbances and the beat results in a higher peak of around 11 or 12 mm Hg and a minimum value of 0 mm Hg.

Figure 4:
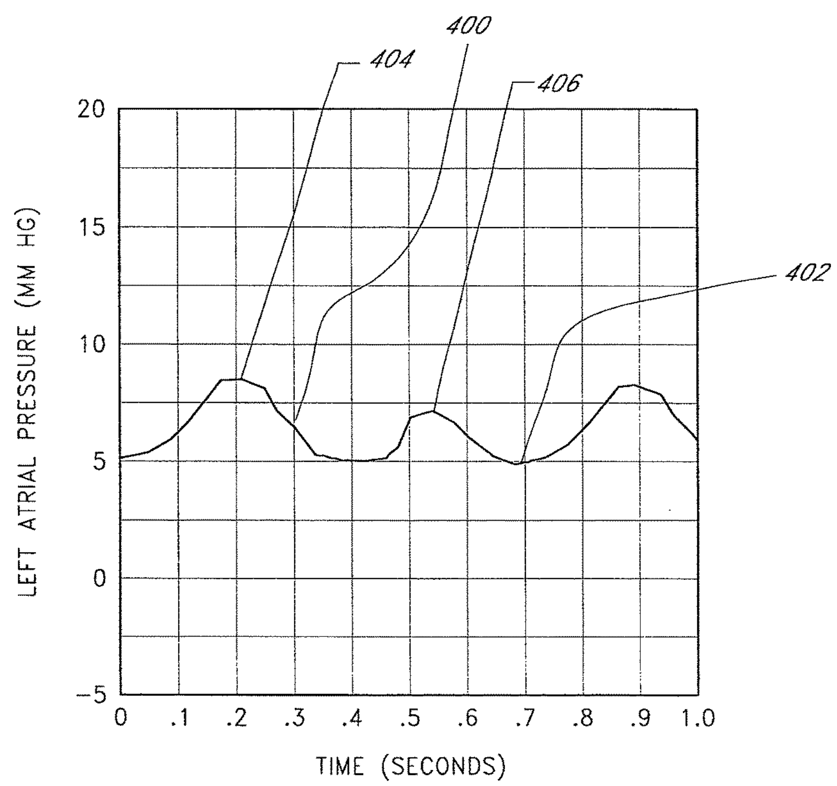
FIG. 4 illustrates a graph of the blood pressure within the left atrium of the heart, as it varies with time.

FIG. 4 illustrates a plot of the left atrial pressure 400 as a function of time. The left atrial pressure 400 is pulsatile and the waveform generally repeats itself each cardiac cycle. The end of the first cardiac cycle 402 is approximately 0.7 seconds following the beginning of the cycle.

Referring to FIG. 4, the left atrial pressure 400, in the illustrated tracing reaches a maximum of 7.5 mm Hg and a minimum of 5 mm Hg. The left atrial pressure 400 pulsatile waveform comprises a larger peak 404 followed by a smaller peak 406 during the course of a single cardiac cycle. The first, larger peak 404 is generated by contraction of the left atrium and the second, smaller peak 406 is generated by contraction of the left ventricle causing retrograde flow into the left atrium and ballooning of the mitral valve into the left atrium.

Figure 5:
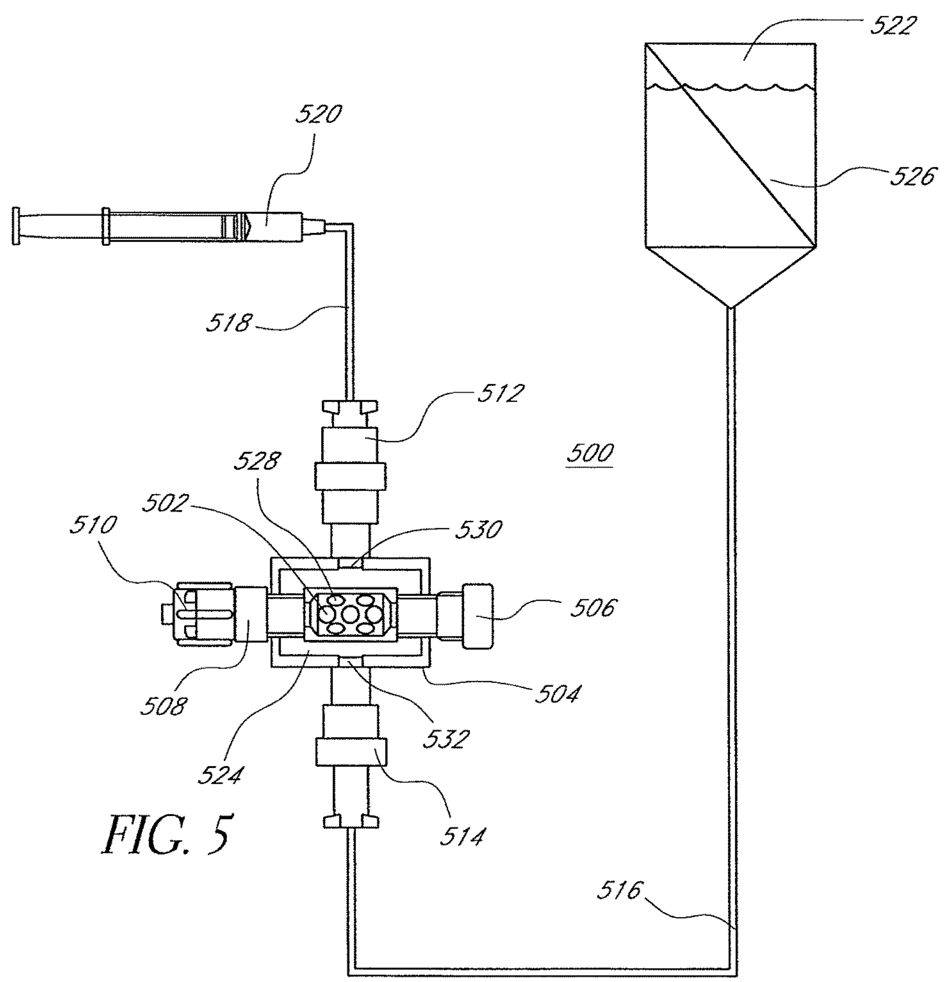
FIG. 5 illustrates a schematic diagram of an embodiment of the air block system.

FIG. 5 illustrates a gas block system 500 comprising a core tube 502, an outer shell 504, a proximal hemostasis valve 506, a distal hemostasis valve 508, a distal connector 510, a reverse flow one way check valve 512, a forward flow one way check valve 514, a fluid inlet line 516, a fluid outlet line 518, an optional fluid withdrawal pump 520, a liquid reservoir 522, an outer shell lumen 524, and a volume of liquid 526. The core tube 502 further comprises a plurality of fenestrations 528. The outer shell 504 further comprises an outlet port 530 and an inlet port 532.

Referring to FIG. 5, the core tube 502 is affixed concentrically within the outer shell 504 at both ends. Both ends of the outer shell 504 where the core tube 502 penetrates are sealed against the passage of fluids from the outer shell lumen 524. The proximal hemostasis valve 506 is affixed to the proximal end of the core tube 502 and the central flow lumen of the proximal hemostasis valve 506 is operably connected to the central lumen of the core tube 502. The distal hemostasis 508 valve is affixed to the distal end of the core tube 502 and the central flow lumen of the distal hemostasis valve 508 is operably connected to the central lumen of the core tube 502. The distal connector 510 is affixed to the distal end of the distal hemostasis valve 508 and the central through lumen of the distal connector 510 is operably connected to the central lumen of the distal hemostasis valve 508. The distal end of the distal connector 510 is reversibly, or permanently, affixed to the proximal end of a catheter hub (not shown). The reverse flow one way check valve 512 is affixed to, and operably connected to, the outlet port 530, which is operably connected to the outer shell 504 and the central lumen of the reverse flow one way check valve 512 is operably connected to the inner lumen 524 of the outer shell 504. The forward flow one way check valve 514 is affixed to and operably connected to the inlet port 532, which is affixed to and operably connected to the outer shell 504. The central lumen of the forward flow one way check valve 514 is operably connected to the inner lumen 524 of the outer shell 504. The fluid inlet line 516 is affixed and operably connected to the central lumen of the forward flow check valve 514 at one end and affixed to and operably connected to the liquid reservoir 522 at the other end. The fluid outlet line 518 is affixed and operably connected to the central lumen of the reverse flow check valve 512 at one end and affixed to and operably connected to the optional fluid withdrawal pump 520 or a reservoir (not shown) at the other end. The volume of liquid 526 fills at least a portion of the liquid reservoir 522, the fluid inlet line 516, the forward flow check valve 514, and the outer shell 504. In one embodiment, the fenestrations 528 are integral to the core tube 502 and are generally breaks or holes in the outer wall of the core tube 502.

The outer shell 504 and the core tube 502 can be fabricated from glass or polymers such as, but not limited to, polycarbonate, polysulfone, polypropylene, polyethylene, polyurethane, polyvinyl chloride, acrylic, polystyrene, or the like. The outer shell 504 and the core tube 502 are preferably fabricated from materials that are transparent and optically clear with a minimum of defects or blemishes. The outer shell 504 and the core tube 502 should be transparent so that bubbles can be visualized or identified by the user such that they can be removed or guided out of the outer shell 504. Some small amount of colorant is acceptable such that a slight blue, violet, green, or yellow tint is present. The outer shell 504 and the core tube 502 can have wall thicknesses that range from 0.020 inches to 0.50 inches, and preferably between 0.040 and 0.250 inches. The reverse flow check valve 512 and the forward flow check valve 514, as well as the proximal hemostasis valve 506, the distal hemostasis valve 508, and the distal connector 510 can be fabricated from the same materials as those used for the outer shell 504. In addition, the valves 512, 514, 506, and 508 can comprise internal seals (not shown) fabricated from flexible or elastomeric polymers such as, but not limited to, polyurethane, silicone elastomer, thermoplastic elastomer, latex rubber, or the like. The fluid inlet line 516 and the fluid outlet line 518 can be fabricated from materials such as, but not limited to, polyvinyl chloride, polyurethane, silicone elastomer, polypropylene, polyethylene, or the like. The fluid reservoir 522 can be a bag or a container such as a bottle, box, or tub fabricated from the same materials as the fluid inlet line 516. The gas removal pump 520 can be a syringe that is manually or mechanically operated or it can be a pump such as a roller pump, a diaphragm pump, a centrifugal pump, a piston pump, or the like. The pump 520 can be manually, electrically, or fluidically powered. In another embodiment, the pump 520 can be a simple fluid reservoir with no active means of pulling a vacuum on the outlet of the reverse flow check valve 512. The pump 520 is advantageously oriented higher than the outer shell 504. The outlet port 530 and the inlet port 532 can be integral to the outer shell 504 or they can be bonded or welded thereto. The outlet port 530 and the inlet port 532 can be perforations in the wall of the outer shell 504.

Figure 6:
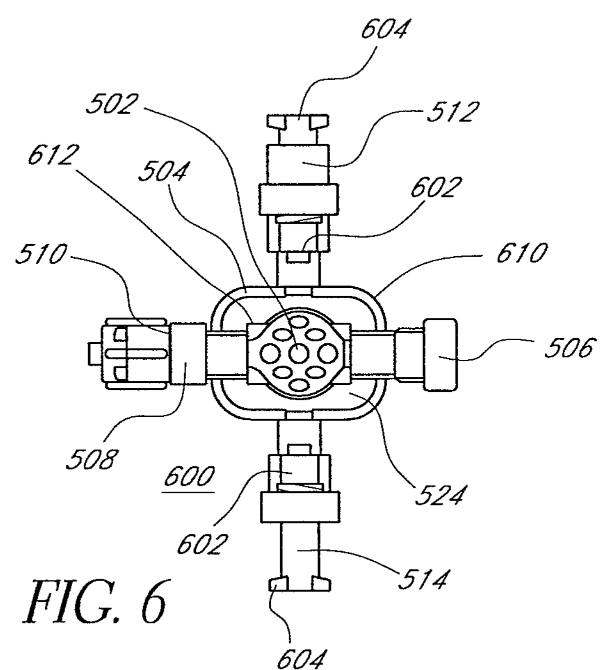
FIG. 6 illustrates an embodiment of the air block without subsystems or catheters.

FIG. 6 illustrates an air block subassembly 600 comprising the core tube 502, the outer shell 504, a proximal hemostasis valve 506, the distal hemostasis valve 508, a distal connector 510, the reverse flow one way check valve 512, the forward flow one way check valve 514, and an outer shell lumen 524. The one way check valves 512 and 514 each further comprise an internal connector 602, and an external connector 604.

Referring to FIG. 6, the internal connector 602 is affixed to the outer shell 504 and the central lumen of the internal connector is operably connected to the central lumen 524 of the outer shell 504 by way of holes in the outer shell 504. In one embodiment, the external connectors 604 are permanently affixed to the outermost edges of the reverse flow check valve 512 and the forward flow check valve 514. The internal connectors 602 and the external connectors 604 can be Luer type connectors, or other bayonet mount or screw mount with a tapered sealing port, for example, suitable for attachment to medical fluid lines and connectors. Referring to FIG. 5, the internal connectors 602 and the external connectors 604 can be fabricated from the same materials as those used to fabricate the outer shell 504.

Figure 7:
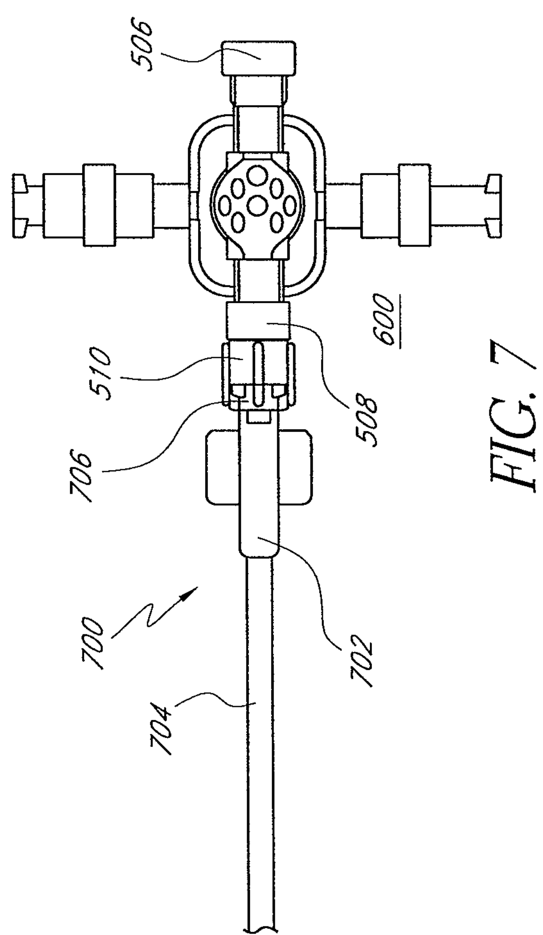
FIG. 7 illustrates an embodiment of the air block connected to a primary catheter.

FIG. 7 illustrates an air block subassembly 600 affixed to a primary catheter 700. The primary catheter 700 comprises a hub 702, a main tube 704, and a hub connector 706. The air block subassembly 600 further comprises the proximal hemostasis valve 506, the distal hemostasis valve 508, and the distal connector 510.

Referring to FIG. 7, the hub 702 is affixed to the main tube 704. In one embodiment, the hub 702 has an integral or attached hub connector 706. The hub connector 706 is permanently or releasably affixed to the distal connector 510 of the air block system 600. The distal connector 510 can be configured to be a device such as, but not limited to, a luer lock, a bayonet mount, a collar with a setscrew, an adhesively coupled connector, a threaded connector, or the like.

Figure 8:
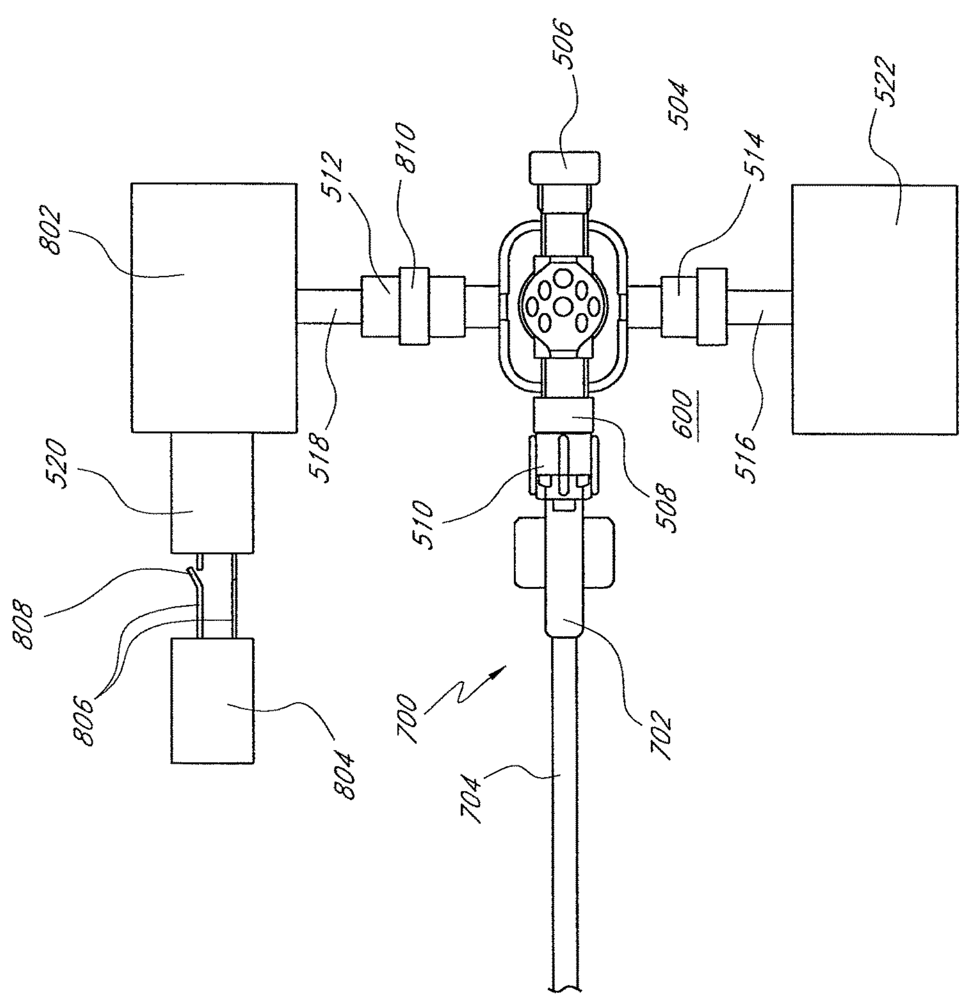
FIG. 8 illustrates an embodiment of the air block connected to a primary catheter with fluid input and gas withdrawal subsystems attached.

FIG. 8 illustrates the air block system 500 affixed to the primary catheter 700. The primary catheter 700 comprises the hub 702 and the main tube 704. The air block system 500 comprises the outer shell 504, the proximal hemostasis valve 506, the distal hemostasis valve 508, the distal connector 510, the reverse flow check valve 512, the forward flow check valve 514, the liquid inlet line 516, the fluid outlet line 518, the fluid withdrawal pump 520, and the liquid reservoir 522. The air block system 500 further comprises an air reservoir 802, a power supply 804, a plurality of power lines 806, a gas permeable membrane 810, and a power switch 808.

Referring to FIG. 8, the air reservoir 802 is affixed to the end of the fluid outlet line 518 that is opposite the end of the fluid outlet line 518 that is connected to the reverse flow one way check valve 512. In an embodiment, the air reservoir 802 can be affixed to the reverse flow one way check valve 512 directly without the intervening fluid outlet line 518. The fluid withdrawal pump 520 is affixed to the air reservoir 802 with or without an intervening fluid line (not shown). The power supply 804 is operably connected to the fluid withdrawal pump 520 using power lines 806. In the illustrated embodiment, there are two power lines 806. A power switch 808 can be operably connected to at least one power line 806 and used to enable power delivery to the fluid withdrawal pump 520 through the power lines 806. In an embodiment, the power supply 804 can be a battery system and the fluid withdrawal pump 520 can be electrically powered.

The fluid removal system can be optimized to selectively withdraw only gasses such as air while leaving liquids behind, within the outer shell 504. In an embodiment, a gas permeable membrane 810 can be operably connected within or about the outlet line 518. The gas permeable membrane 810 is a filter comprising, for example, a microporous membrane fabricated from materials such as, but not limited to, polypropylene, polyethylene, polytetraflouoroethylene, other polyolefin, polyester, or the like. The membrane can have porous structures that penetrate from one side of the membrane to the other. The size of the pores can be about 100 microns with a range of about 50 microns to about 1000 microns. The pore density and pore size can be selected to be compatible with a pressure drop across the membrane, as generated by the pump 520 or other suction (vacuum) or pressure generating device, so as to remove a given volume of air over a reasonable length of time, for example 1-cc in 5 minutes, while preventing the loss of blood or other liquids from the system.

Figure 9:
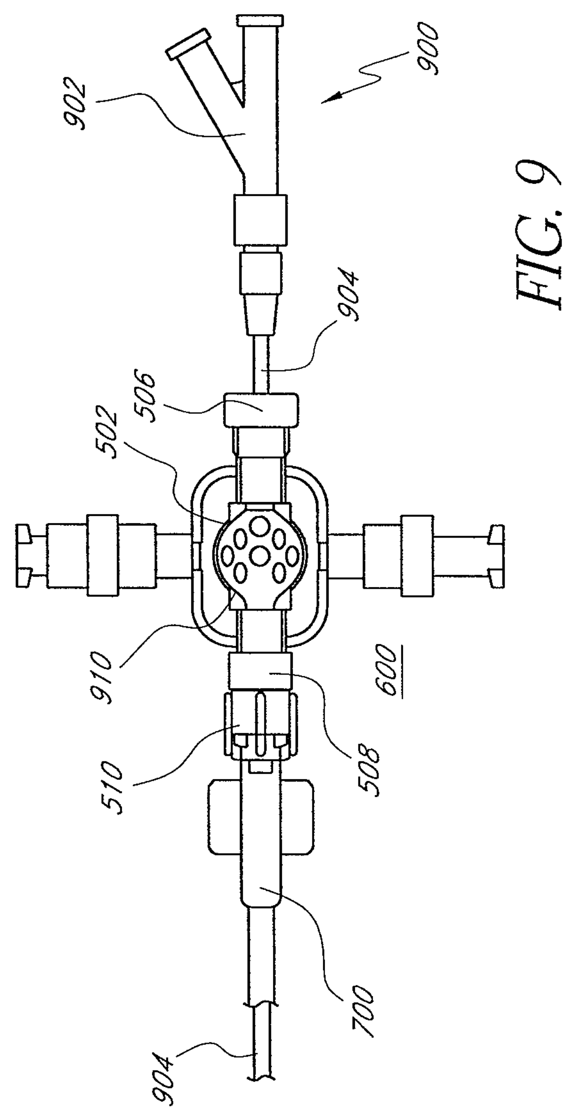
FIG. 9 illustrates an embodiment of the air block connected to a primary catheter with a secondary catheter inserted therethrough.

FIG. 9 illustrates the air block subassembly 600 comprising the proximal hemostasis valve 506, the distal hemostasis valve 508, and the distal connector 510 affixed to the primary catheter 700. The air block subassembly 600 comprises the perforated core tube 502 which further comprises an interior distal surface 910 that is smooth and gently sloped. A secondary catheter 900 is inserted through the air block subassembly 600 and the primary catheter 700. The secondary catheter 900 comprises a hub 902 and a main tube 904.

Referring to FIG. 9, the main tube 904 of the secondary catheter 900 is affixed to the hub 902 and one or more lumens within the main tube 904 are operably connected to one or more lumens in the hub 902. The main tube 904 of the secondary catheter 900 is slidably inserted through the proximal hemostasis valve 506, the air block system 600, and the central lumen of the primary catheter 700. The proximal hemostasis valve 506 and the distal hemostasis valve 508 operably seal against the passage of fluids around the exterior surface of the main tube 904. The inner surfaces of the core tube 502 are smooth and without bumps, especially on the distal end 910 of the core tube, so that the secondary catheter 900, when inserted in the distal direction, does not hang up or catch on ridges, bumps, or ledges. The interior surface of the distal end 910 of the core tube 502, when tapering from a larger to a smaller diameter when moving in the distal direction, beneficially has a relatively gentle angle of 1 to 45 degrees to facilitate advancement of the secondary catheter 900, especially if the secondary catheter 900 comprises radial enlargements or a curvature or bend at right angles to the longitudinal axis. Such gentle tapering and lack of bumps or ridges can also be present on the proximal end of the core tube 502 inner surface, and can reduce friction on a secondary catheter 900 which has radial enlargements while it is being withdrawn proximally through the core tube 502.

Figure 10:
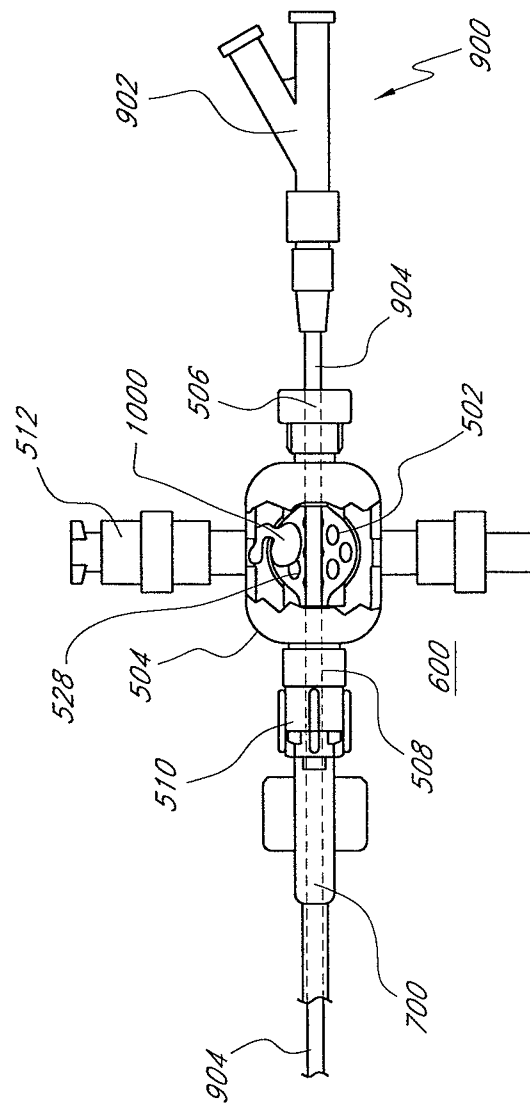
FIG. 10 illustrates a close up view of an embodiment of the air block showing a catheter inserted therethrough and a bolus of air being drawn out of the core tube into the lumen of the outer shell.

FIG. 10 illustrates the air block subassembly 600 affixed to the primary catheter 700 with the main tube 904 of the secondary catheter 900 inserted through both the air block subassembly 600 and the primary catheter 700. The air block subassembly 600 comprises the core tube 502 further comprising the plurality of fenestrations 528, the outer shell 504, the proximal hemostasis valve 506, the distal hemostasis valve 508, and the distal connector 510. A bolus of air 1000 has escaped into the air block assembly 600 and is being removed from the lumen of the core tube 502, through the fenestrations 528, into the lumen of the outer shell 504.

Referring to FIG. 10, an air bubble 1000 is shown trapped within the lumen of the core tube 502. The air bubble 1000 is shown moving upward toward the reverse flow check valve 512 due to buoyancy forces generated by gravity acting on the bubble 1000 and the liquid within the air block system 600. The air bubble 1000 will ultimately move out of the core tube 502 altogether where it will reside within the outer shell 502 prior to being withdrawn out through the reverse flow check valve 512 and away from the blood path.

Figure 11:
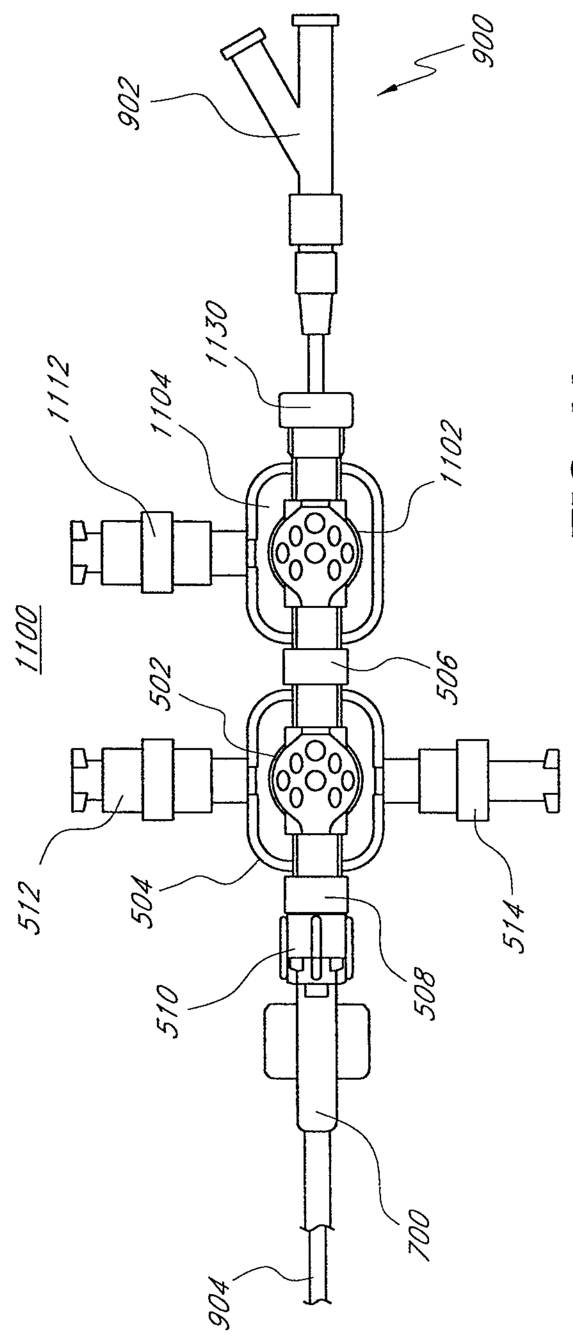
FIG. 11 illustrates a side view of an embodiment of an air block or air block that utilizes a dual chamber design.

FIG. 11 illustrates a side cross-sectional view of a dual chamber air block 1100. The dual chamber air block 1100 comprises the first outer shell 504, the first core tube 502, the distal hemostasis valve 508, the proximal hemostasis valve 506, the reverse flow check valve 512, the forward flow check valve 514, the distal coupler 510, the primary catheter 700, and the secondary catheter 900 further comprising the secondary catheter hub 902 and the secondary catheter tube 904. The dual chamber air block 1100 further comprises a second outer shell 1104, a second core tube 1102, a second reverse flow check valve 1112, and a second proximal hemostasis valve 1130.

Referring to FIG. 11, the distal end of the second core tube 1102 is affixed to and its central lumen is operably connected to the proximal end of the proximal hemostasis valve 506. The second proximal hemostasis valve 1130 is affixed to and its through lumen is operably connected to the central lumen of the second core tube 1102. The second reverse flow check valve 1112 is affixed to the second outer shell 1104 and its central lumen operably connected to the internal lumen of the second outer shell 1104 by way of a fenestration or outlet port in the second outer shell 1102. A pressurized liquid source is operably connected to the forward flow check valve 514 or it is directly connected to the interior volume of the first outer shell 504.

Referring to FIGS. 11 and 5, the sizes of the two chambers of the dual chamber air block 1100 can be approximately the same, or they can vary by as much as 80% in volume. The forward flow check valve 514 can be operably connected to the pressurized source 522 of liquid 526. The liquid 526 can be delivered at pressures of between 20 and 300 mm Hg. It is preferable that the liquid 526 be biologically compatible fluid such as, but not limited to, ringers solution, isotonic saline, heparinized saline, or the like. The liquid 526 can be sterilized and delivered through a sterile system to prevent infection to a patient. The liquid 526, delivered at a pressure higher than that of the central venous circulation, will flow both distally and proximally, if allowed, within the first outer shell 504 and the second outer shell 1104. The movement of the liquid 526 is controlled by the distal hemostasis valve 508, the proximal hemostasis valve 506, and the second proximal hemostasis valve 1130. Should air be entrained into the second outer shell 1104 through the second proximal hemostasis valve 1130, the high pressure within the first outer shell 504 will prevent entrance of the air into the first outer shell through any potential opening or defect in the proximal hemostasis valve 506. A leak or defect in the distal hemostasis valve 508 could result in the flow of the liquid 526 through the first catheter 700 and into the patient, but since the liquid 526 is biocompatible, this event will have no adverse clinical effect. Any air that does become trapped within the system can be drawn out through the reverse flow check valve 512 or the second reverse flow check valve 1112. In other embodiments, the forward flow check valve 514 can be eliminated and the line 516 can be directly connected to the outer shell 504. In another embodiment, one or more of the reverse flow check valves 512 or 1112 can be eliminated and replaced by gas permeable membranes, or simply be connected to the fluid withdrawal line 518.

Referring to FIGS. 5, 6, 7, and 11, the volume of the outer shell 504 or 1104 can vary between 0.5 cubic centimeter (cc) and 100-cc. The size of the system is beneficially reduced to allow the system 500, 600, or 1100 to be connected to a primary catheter 700 and still be maneuvered without encumbering the user or hindering manipulation. The air block system 500 is beneficially sterilized prior to use to prevent infection to a patient.

Referring to FIG. 5, an air block apparatus 500 is disclosed herein, which prevents air from passing through a catheter, cannula, or sheath into a patient's cardiovascular system, wherein the air block 500 comprises an outer shell 500, further comprising a wall and an inner lumen 524 having a proximal end and a distal end, a core tube 502 comprising an axially elongate wall, an inner lumen, and a plurality of fenestrations 528, wherein the core tube 502 resides within the outer shell 504 and is sealed to the outer shell 504 at its proximal end and its distal end, a first hemostasis valve 506 affixed to the core tube 502 at the proximal end of the core tube, a second hemostasis valve 508 affixed to the core tube 502 at the distal end of the core tube 502, and an outlet port 530 affixed to the wall of the outer shell 504, wherein the outlet port 530 is operably connected to the inner lumen 524 of the outer shell 504, wherein the fenestrations 528 in the wall of the core tube 502 are large enough to permit air or other gas to pass out of the core tube 502 and into the inner lumen 524 of the outer shell.

In another embodiment, the air block apparatus can further comprise an inlet port 532 affixed to the wall of the outer shell 504, wherein the inlet port 532 is operably connected to the inner lumen 524 of the outer shell 504. In another embodiment, the air block apparatus can further comprise an inlet port 530 operably connecting the inner lumen 524 of the outer shell with a source 522 of liquid 526. The apparatus can also comprise a vacuum source 520 operably connected to the outlet port 530, wherein the vacuum source 520 removes gas from the inner lumen 524 of the outer shell 504. Referring to FIGS. 5 and 8, the air block apparatus 500 can comprise a gas permeable membrane 810 operably connected between the vacuum source 520 and the outlet port 530, wherein the gas permeable membrane 810 permits the removal of gas from the inner lumen 524 of the outer shell 504 while substantially preventing the removal of liquid from the inner lumen 524 of the outer shell 504. Referring to FIG. 6, the air block apparatus 500 can also have a core tube 502 that further comprises a central bulge 610 extending radially outward such that when the inner lumen 524 is oriented perpendicular to the line of gravity, gas moves radially away from the central axis of the core tube 502 toward the outer wall, where it is able to pass into the inner lumen of the outer shell through fenestrations 528 in the wall of the core tube 502.

The core tube 502 of the air block 600 can comprise a central bulge 610 extending radially outward, wherein said central bulge 610 is gently tapered along the inner distal surface 612 of the outer wall of the core tube 502 such that a catheter inserted therethrough, from the proximal end, does not catch, but is guided into the smaller diameter regions of the core tube without catching or hanging up as it is advanced distally. In another embodiment, the first, proximal hemostasis valve 506 of the apparatus is configured to receive a catheter and seal around said catheter when the catheter is inserted therethrough and further wherein the proximal hemostasis valve 506 is configured to seal substantially against the flow or air or liquid when nothing is inserted therethrough. The second hemostasis valve 508 can be configured to receive a catheter and seal around said catheter when the catheter is inserted therethrough and further wherein the distal, or second hemostasis valve 508 is configured to seal substantially against the flow or air or liquid when nothing is inserted therethrough. Referring to FIGS. 6 and 7, the air block apparatus 600 can further comprise an adapter 510 to permit attachment of the distal end of the second hemostasis valve 508 to a hub 702 of a catheter 700 such that the central lumen of the core tube 502 is operably connected to the inner lumen of the hub 702 of the catheter or sheath 700 as permitted by the second hemostasis valve 508. The adapter 510 can be configured to permit removable attachment of the air block apparatus 600 to the hub of the catheter 700.

Referring to FIGS. 5, 6, 7, and 9, in another embodiment, a method of preventing substantial infusion of air into the proximal end of a first catheter 700 is disclosed, the method comprising the steps of affixing an air block 600 having a longitudinal axis to the proximal end of a first catheter 700, wherein the air block comprises an outer shell 504, a fenestrated core tube 502, a first hemostasis valve 506, a second hemostasis valve 508, an inlet port 532, and an outlet port 530, affixing a source 522 of sterile liquid 526 to the inlet port, affixing a gas withdrawal system 520 to the outlet port, inserting a secondary catheter 900 through the air block into the first catheter or sheath 700, wherein the first and second hemostasis valves 506 and 508 prevent air from entering or escaping the air block 600, orienting the air block 600 such that its longitudinal axis is substantially horizontal relative to the pull of gravity; and removing gas bubbles that collect between the outer shell 504 and the fenestrated core tube 502 such that the gas bubbles no longer reside within the outer shell 504.

The method can further comprise the step of elevating the source 522 of sterile liquid 526 above the level of the outer shell 504. The method can also comprise the step of activating a pump 520 to remove the gas from the outer shell 504 through the outlet port 530. In another embodiment, the method can further comprise the step of removing the gas from the outer shell 504 through a gas permeable membrane 810 which is operably connected to the outlet port 530. The method can involve replacement of the secondary catheter 900 with a guidewire at one or more points in the procedure. The method can further comprise the step of collecting the removed gas in a holding chamber 802, which can be a separate structure or integral to the block 500. In another embodiment, the method can comprise the step of returning any liquid, which was unintentionally removed from the system, back into the outer shell 504 through the inlet port 532.

The method can comprise the step of sterilizing the air block 500 or 600 prior to attaching it to the first catheter, sheath, or introducer 700. The method can also comprising the step of packaging the air block 500 or 600 within a kit, wherein the kit comprises at least the first catheter or sheath 700 and the air block 500, 600. The method can comprise pre-affixing the air block to the hub 702 of the first catheter, sheath, introducer, or cannula 700. The method of can comprise the step or steps of providing therapeutic intervention within the cardiovascular system wherein the instrumentation is placed through the air block apparatus 500, 600 into the sheath or first catheter 700. The method can comprise the step or steps of providing diagnostic intervention within the cardiovascular system through the air block apparatus 500, 600. The method can comprise routing the first catheter or sheath 700 to the right atrium of the heart through the venous system. Subsequent steps can involve passing the first catheter or sheath 700 through the interatrial septum and resides, at its distal end, within the left atrium of the heart.

In another embodiment, an apparatus 1100 is disclosed, which is adapted for preventing substantial infusion of air into the proximal end of a first catheter 700 comprising means for collecting air within a primary inner chamber 502, means for collecting air within a primary outer chamber 504, means for permitting the air to move from the primary inner chamber 502 to the primary outer chamber 504, means for inserting a catheter 900 through the inner chamber 502, means 506 for preventing substantial air from entering the primary inner chamber 502 from the proximal end of the primary inner chamber 502, means 508 for preventing substantial air from leaving the primary inner chamber 502 at its distal end while still permitting passage of a catheter 900 therethrough, means for infusion of liquid into the primary outer chamber 504, and means for removal of gas from the primary outer chamber 504. The apparatus 1100 can further comprise a secondary, perforated, inner chamber 1102 surrounded by a secondary outer chamber 1104, a means 1112 for removing air from the secondary outer chamber 1104, and a secondary proximal hemostasis valve 1130, wherein said secondary, or second, inner and outer chambers 1102 and 1104, respectively, positioned proximally to the primary inner chamber 502 and operably separated from the primary outer chamber 504 by a means 506 to permit catheter passage between the primary 502 and secondary 1102 inner chambers while substantially prohibiting the flow of fluids between said primary 502 and secondary 1102 inner chambers.

An air block apparatus 500, 600, 1100 is disclosed herein, which is adapted for preventing air from passing from a room through a catheter, sheath, cannula, or introducer 700 into a patient's cardiovascular system comprising an outer shell 504 comprising a wall and an inner lumen having a proximal end and a distal end, a core tube 502 comprising an axially elongate wall, an inner lumen, and a plurality of fenestrations 528, wherein the core tube 502 resides within the outer shell 504 and is sealed to the outer shell 504 at its proximal end and its distal end, a first valve 506 affixed to the inner lumen of the core tube 502 at the proximal end of the core tube 502, wherein said first valve 506 permits the passage of a catheter 900 but substantially prohibits the flow of fluids, either liquid or room air, therethrough, a second valve 508 affixed to the inner lumen of the core tube 502 at the distal end of the core tube 502, wherein said second valve 508 permits the passage of a catheter 900 but substantially prohibits the flow of fluids, either liquid or room air therethrough, an outlet port 530 for withdrawing any gas, including room air, collected in the outer shell 504, away from the outer shell 504, and a source 522 of sterile, biocompatible liquid 526 delivered at a pressure greater than central venous pressure, wherein the source 522 of sterile, biocompatible liquid 526 is operably connected to the inner lumen 524 of the outer shell 504, wherein the sterile biocompatible liquid 526 is delivered at a pressure higher than that of the room air and substantially prevents the flow of room air from the first valve 506 into the inner lumen of the core tube 502.

An air block apparatus 500, 600, 1100 is disclosed, which is adapted for preventing gas from passing from a room environment through a catheter 700 into a patient's cardiovascular system comprising a chamber 504 affixed to the proximal end of a first catheter 700, wherein the chamber 504 is operably connected to a source 522 of liquid 526 which is pressurized to a level above that of the pressure within the cardiovascular system, a first valve 506 affixed to the proximal end of the chamber 504, wherein said first valve 506 permits insertion of a second catheter 900 from a room environment through the first valve 506 and into the chamber 504, and a second valve 508 affixed to the distal end of the chamber 504, wherein said second valve 508 permits insertion of the second catheter 900 from the chamber 504, through the second valve 508, into the proximal end the first catheter 700, wherein the first valve 506 and the second valve 508 are configured to permit catheter 900 passage but substantially prohibit the passage of air, from the room environment, therethrough.

In one embodiment, the cross-sectional area of the outer shell 504 is substantially larger than the cross-sectional area of the catheter 700. In one embodiment, the cross-sectional area of the outer shell 504 is at least three times greater than the cross-sectional area of the catheter 700. In yet other embodiments, the cross-sectional area of the outer shell 504 is at least two times greater than the cross-sectional area of the catheter 700.

In another embodiment, the diameter of the outer shell 504 is substantially larger than the diameter of the catheter 700. In one embodiment, the diameter of the outer shell 504 is at least three times greater than the diameter area of the catheter 700. In yet other embodiments, the diameter of the outer shell 504 is at least two times greater than the diameter of the catheter 700.

Figure 12:
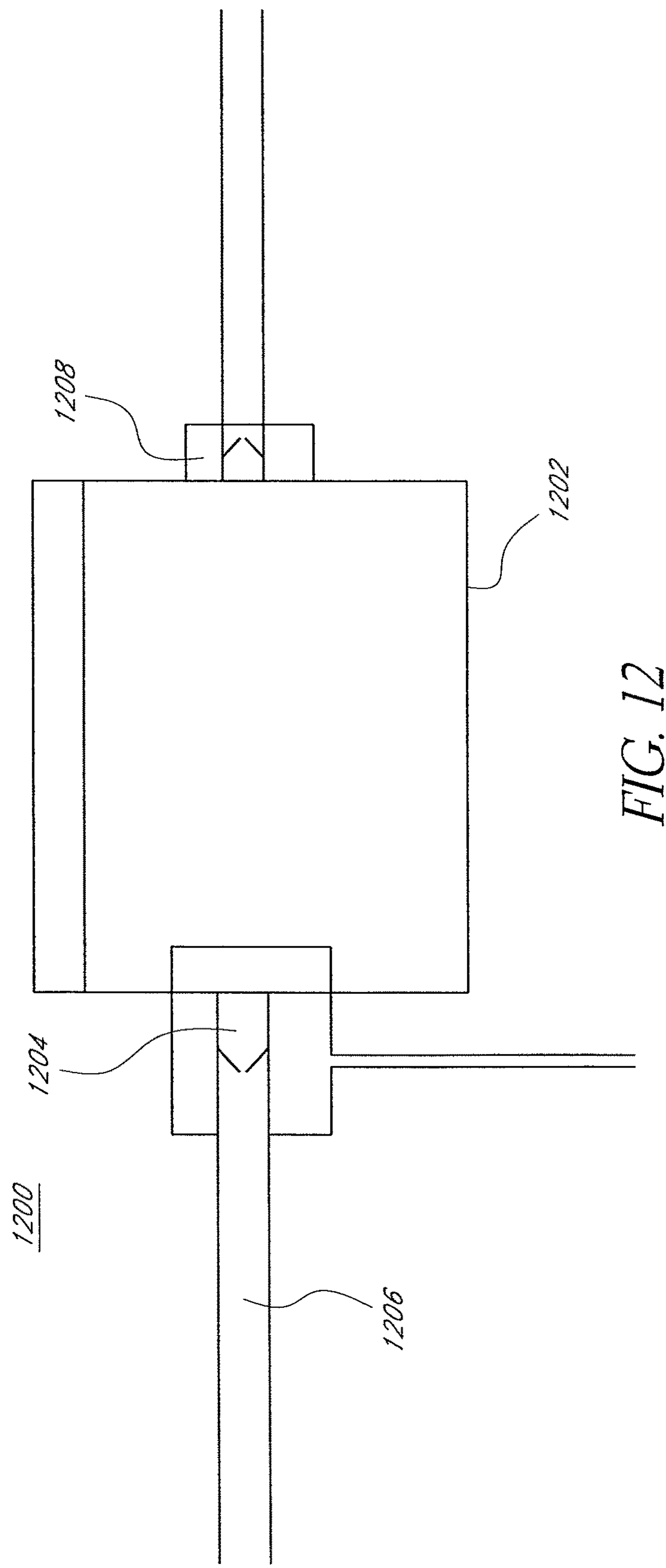
FIG. 12 illustrates an embodiment of an air embolism prevention device.

FIG. 12 illustrates an air embolism prevention device, or air block 1200, comprising a shell 1202, an exit valve 1204, an intravascular sheath 1206, and a catheter insert port 1208. The air embolism prevention device 1200 prevents air bubbles from entering the intravascular sheath 1206 during any heart procedure, left-sided or right-sided. Air bubbles that get introduced into the vasculature could cause stroke, myocardial infarct, or other ischemic event. The shell 1202 is affixed to the intravascular sheath 1206 by a coupler (not shown) or it is permanently attached by bonding, welding, or the like. The catheter insert port 1208 is affixed to the proximal end of the shell 1202. The exit valve 1204 is affixed to the distal end of the shell 1202 and is coupled, at or near its distal end, to a point substantially near the proximal end of the intravascular sheath 1206. The exit valve 1204 is operably connects the through lumen of the intravascular sheath 1206 to the internal volume of the shell 1202 under control of the valving mechanism within the exit valve 1204. The insert port 1208 operably connects the external environment with the interior volume of the shell 1202.

Figure 13:
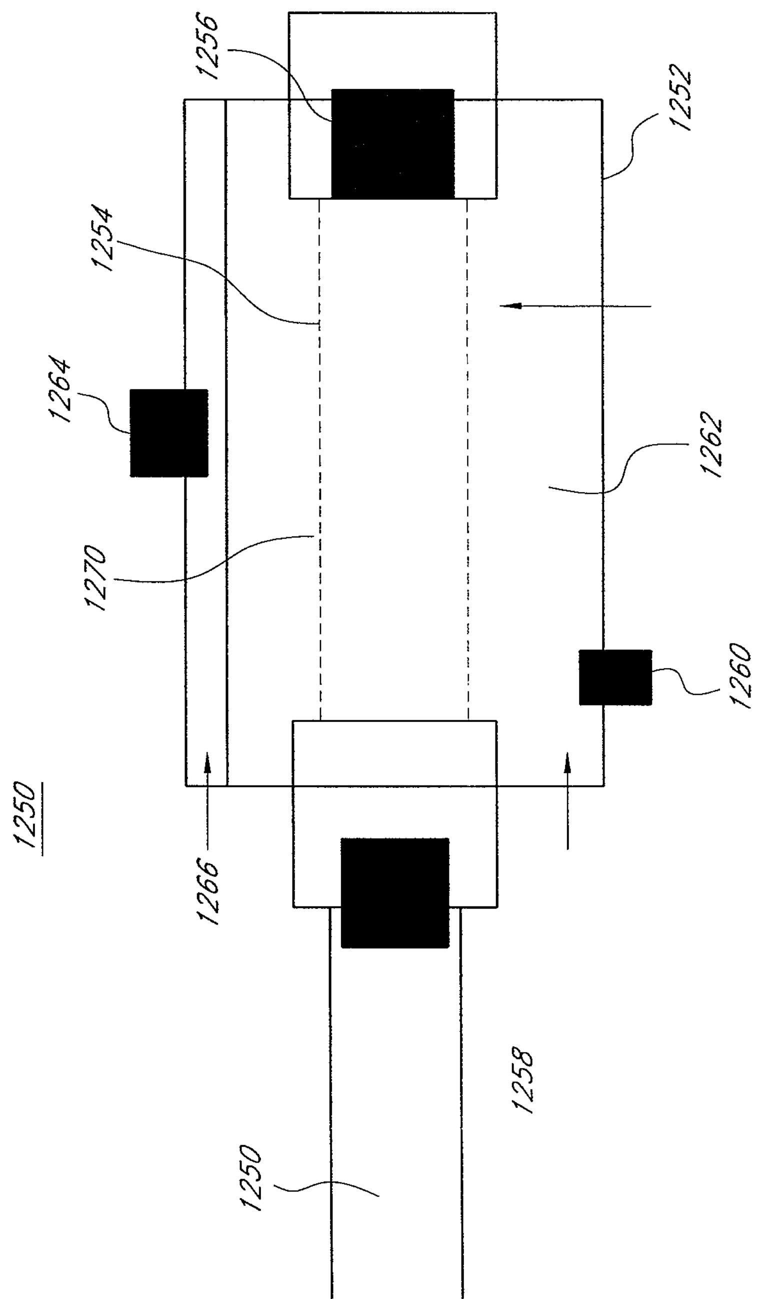
FIG. 13 illustrates an embodiment of a system of preventing air embolism during vascular procedures.

FIG. 13 illustrates a system and method of preventing air embolism during vascular procedures. The system, an air block or trap 1250, comprises a case 1252, a perforated cylindrical track 1254 further comprising fenestrations or perforations 1270, an inlet valve 1256, an outlet valve 1258, an infusion port 1260 for a volume of pressurized liquid 1262, an air escape valve 1264, the volume of liquid 1262, a volume of collected air 1266, and a medical introducer sheath 1268. The perforated cylindrical track 1254 allows catheter (not shown) passage and guide catheter (not shown) use when guidewires (not shown) have been introduced through the medical introducer sheath 1268. The perforated cylindrical track 1254 further allows any air collected 1266 within its lumen to escape through the perforations 1270 into the surrounding chamber defined by annulus between the shell or case 1252 and the perforated cylindrical track 1254. The pressurized infusion port 1260 prevents bleed out and air entry, maintaining a fluid (saline) interface at all times when the medical introducer sheath 1268 is used. The entire air block 1250 can be attached or affixed to a medical introducer sheath 1268, catheter, cannula, or the like by way of a coupler (not shown) which engages, either permanently or removably, at or near the proximal end of the sheath 1268 hub (not shown). The inlet valve 1256 and the outlet valve 1258 are preferably hemostasis type valves, such as those known in the art of medical devices.

The present invention may be embodied in other specific forms without departing from its spirit or essential characteristics. The described embodiments are to be considered in all respects only as illustrative and not restrictive. For example, the gas withdrawal system can be powered by an external power source or it can be powered manually. The scope of the invention is therefore indicated by the appended claims rather than the foregoing description. All changes that come within the meaning and range of equivalency of the claims are to be embraced within their scope.

What is claimed is:

1. An air block apparatus, comprising:

an outer shell defining an interior volume and having a proximal end and a distal end;

a core tube located within the interior volume of the outer shell and extending along an axis from the proximal end of the outer shell to the distal end of the outer shell, the core tube comprising an unobstructed inner channel extending from the proximal end to the distal end and configured to receive an instrument therethrough along the axis, the core tube having a fenestrated portion that is configured to permit gas to move out of the inner channel of the core tube and into the interior volume of the outer shell;

a first valve operably connected to the inner channel of the core tube towards the proximal end of the core tube;

a second valve operably connected to the inner channel of the core tube towards the distal end of the core tube;

a first port operably connected to the interior volume of the outer shell and configured to pass liquid into the interior volume of the outer shell; and a second port operably connected to the interior volume of the outer shell and configured to pass at least gas out of the interior volume of the outer shell.

2. The air block apparatus of claim 1 wherein the core tube further comprises a bulge extending radially outward from a central axis of the core tube.

3. The air block apparatus of claim 2 wherein the central bulge is tapered along the inner surface of the core tube.

4. The air block apparatus of claim 1, wherein the first valve is configured to permit passage of a catheter therethrough and into the inner channel of the core tube.

5. The air block apparatus of claim 1, wherein the second valve is configured to permit passage of a catheter therethrough and into the inner channel of the core tube.

6. The air block apparatus of claim 1, wherein the first valve is a hemostasis valve and the second valve is a hemostasis valve.

7. The air block apparatus of claim 1 further comprising a gas permeable membrane operably connected between a vacuum source and the second port, wherein the gas permeable membrane permits the removal of gas from the interior volume of the outer shell while substantially preventing the removal of liquid from the interior volume of the outer shell.

8. The air block apparatus of claim 1 wherein the first valve is configured to receive a catheter and to seal around the catheter when the catheter is inserted therethrough, and further wherein the first valve is configured to seal substantially against the flow of air or liquid when nothing is inserted therethrough.

9. The air block apparatus of claim 1 wherein the second valve is configured to receive a catheter and seal around the catheter when the catheter is inserted therethrough and further wherein the second valve is configured to seal substantially against the flow of air or liquid when nothing is inserted therethrough.

10. The air block apparatus of claim 1 further comprising an adapter to permit removable attachment of a distal end of the second valve to a hub of a catheter.

11. The air block apparatus of claim 1, wherein the first and second ports are on opposite sides of the outer shell and aligned along an axis generally perpendicular to the axis of the core tube.

* * * * *